(12) United States Patent
Daniel et al.

(10) Patent No.: US 11,633,284 B2
(45) Date of Patent: Apr. 25, 2023

(54) FOLD-UP CONTAINMENT DEVICE FOR BONE DEFECTS

(71) Applicant: DePuy Synthes Products, Inc., Raynham, MA (US)

(72) Inventors: Steffan Daniel, Zuchwil (CH); André Furrer, Zuchwil (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 17/305,031

(22) Filed: Jun. 29, 2021

(65) Prior Publication Data

US 2021/0322171 A1 Oct. 21, 2021

Related U.S. Application Data

(62) Division of application No. 15/801,528, filed on Nov. 2, 2017, now abandoned.
(Continued)

(51) Int. Cl.
*A61F 2/28* (2006.01)
*A61B 17/80* (2006.01)
*A61F 2/30* (2006.01)

(52) U.S. Cl.
CPC ........ *A61F 2/2846* (2013.01); *A61B 17/8071* (2013.01); *A61B 17/8085* (2013.01); *A61F 2/2803* (2013.01); *A61F 2/30942* (2013.01); *A61F 2002/30072* (2013.01); *A61F 2002/3092* (2013.01); *A61F 2002/30131* (2013.01);
(Continued)

(58) Field of Classification Search
CPC .......... A61F 2/2846; A61F 2002/30576; A61F 2/2803; A61F 2002/2835; A61F 2002/3092; A61F 2002/30537; A61F 2002/30588; A61F 2002/30261; A61F 2002/30271; A61B 17/8071; A61B 17/8085
See application file for complete search history.

(56) References Cited

U.S. PATENT DOCUMENTS 3,720,959 A 3/1973 Hahn
4,718,916 A 1/1988 Morscher
(Continued)

FOREIGN PATENT DOCUMENTS

CN 103221001 7/2013
EP 0615728 9/1994
(Continued)

*Primary Examiner* — Javier G Blanco
(74) *Attorney, Agent, or Firm* — Fay Kaplun & Marcin, LLP

(57) ABSTRACT

A bone graft system includes a two-dimensional mesh sheet sized and shaped to, when folded along fold lines, form a three-dimensional graft containment structure configured to be packed with a bone graft material for placement within a target area of a bone, the mesh sheet including a first end flap connected to a remaining portion of the mesh sheet via a first fold line and a second end flap connected to the remaining portion of the mesh sheet via a second fold line, a third fold line extending from the first fold line to the second fold line so that the remaining portion is configured to be wrapped around folded first and second end flaps to form the graft containment structure, the first and second end flaps substantially corresponding to a profile of the target area of the bone.

11 Claims, 5 Drawing Sheets

Related U.S. Application Data

(60) Provisional application No. 62/417,052, filed on Nov. 3, 2016.

(52) U.S. Cl.
CPC ............... *A61F 2002/30153* (2013.01); *A61F 2002/30261* (2013.01); *A61F 2002/30326* (2013.01); *A61F 2002/30537* (2013.01); *A61F 2002/30576* (2013.01); *A61F 2002/30578* (2013.01); *A61F 2002/30784* (2013.01)

(56) References Cited

U.S. PATENT DOCUMENTS

| | | |
|---|---|---|
| 5,443,483 A | 8/1995 | Kirsch |
| 5,503,164 A | 4/1996 | Friedman |
| 5,919,234 A | 7/1999 | Lemperle et al. |
| 6,719,735 B1 | 4/2004 | Cornwall et al. |
| 2002/0130093 A1* | 9/2002 | Ferrara, Jr. .......... B65D 5/4233 211/49.1 |
| 2005/0169893 A1* | 8/2005 | Koblish ................ A61L 27/54 424/602 |
| 2005/0273165 A1 | 12/2005 | Griffiths et al. |
| 2009/0275962 A1 | 11/2009 | Zeiner et al. |
| 2010/0215718 A1* | 8/2010 | Swords ................ A61L 27/56 424/549 |
| 2011/0035024 A1 | 2/2011 | Malmquist et al. |
| 2013/0327667 A1* | 12/2013 | Grabowski .......... B65D 5/4204 53/467 |
| 2016/0235537 A1* | 8/2016 | Magagnoli ............... B28B 1/24 |
| 2017/0239050 A1* | 8/2017 | Vickers ................ A61L 27/54 |
| 2018/0193530 A1 | 7/2018 | Barbas et al. |

FOREIGN PATENT DOCUMENTS

| | | | |
|---|---|---|---|
| JP | 2008501435 A | 1/2008 | |
| JP | 3184817 U | 7/2013 | |
| WO | 88/01517 | 3/1988 | |
| WO | 2012/036129 A1 | 3/2012 | |
| WO | WO-2018069918 A1 * | 4/2018 | .......... A61C 8/0006 |

* cited by examiner

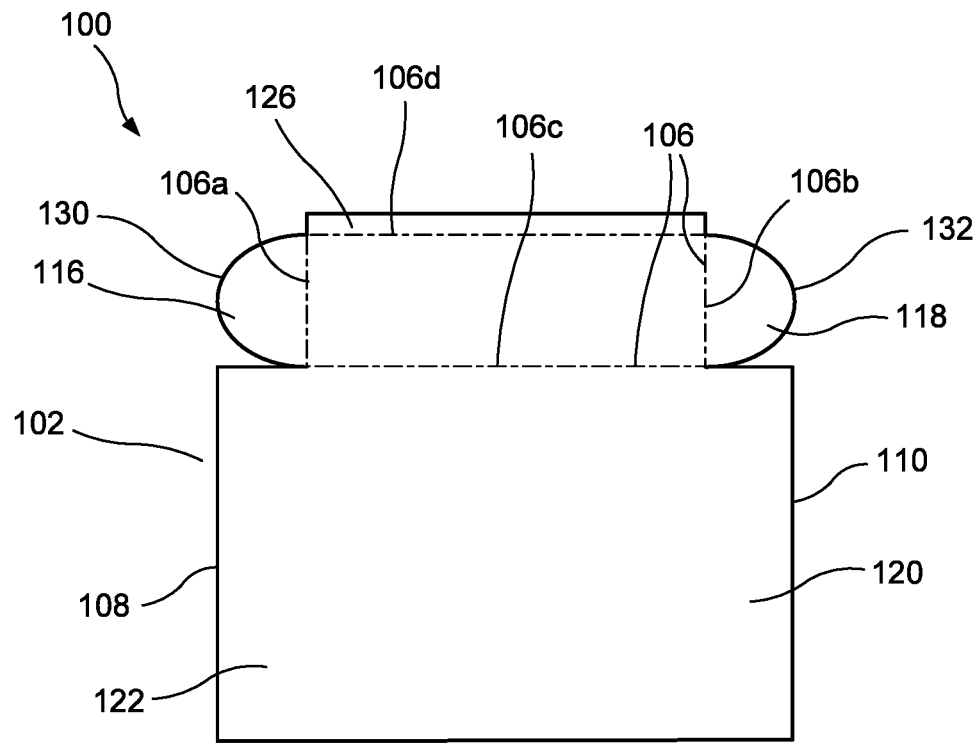
F I G. 1
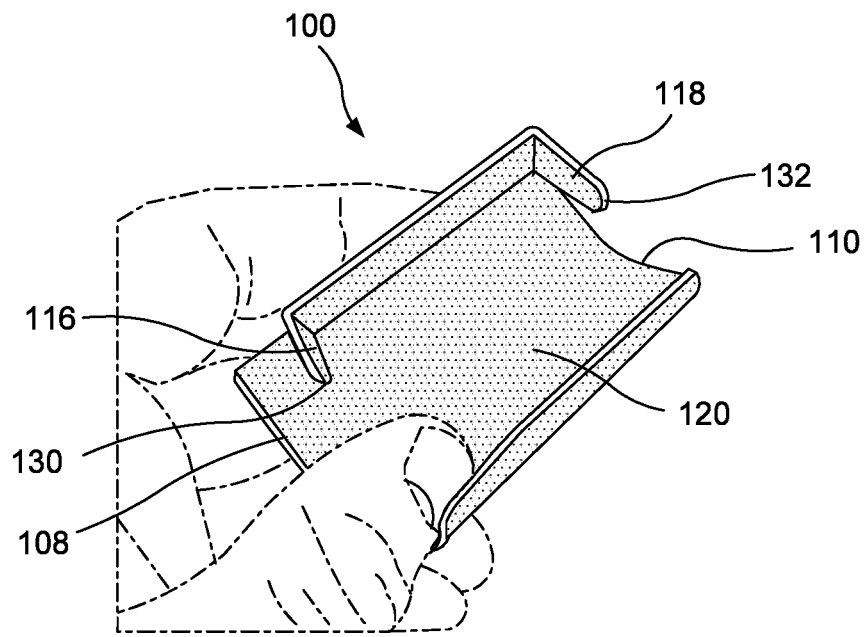
F I G. 2

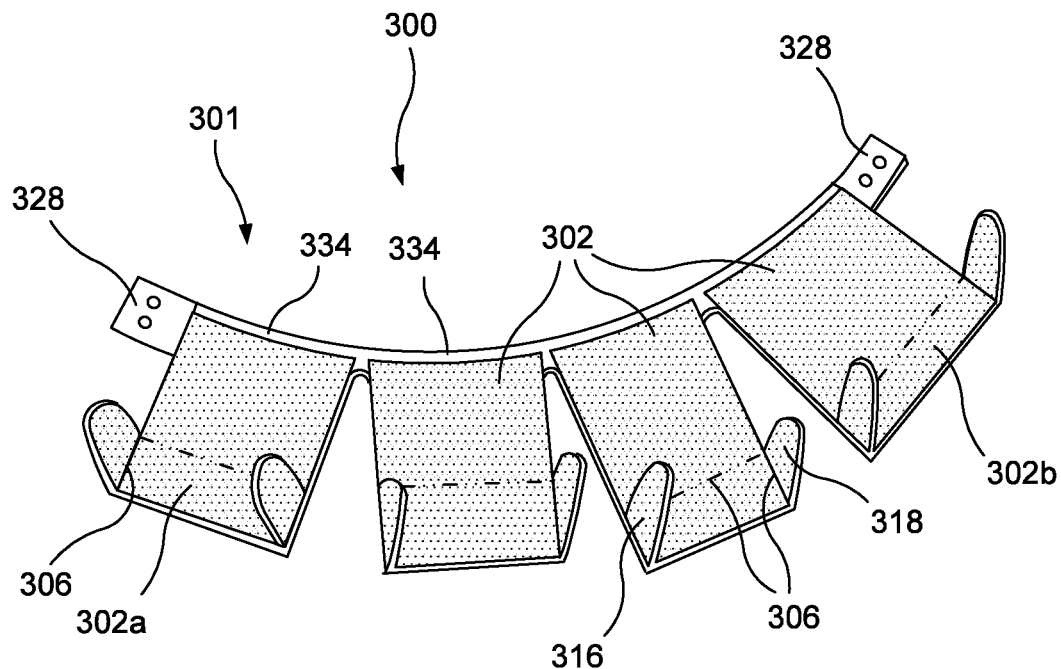
F I G. 7
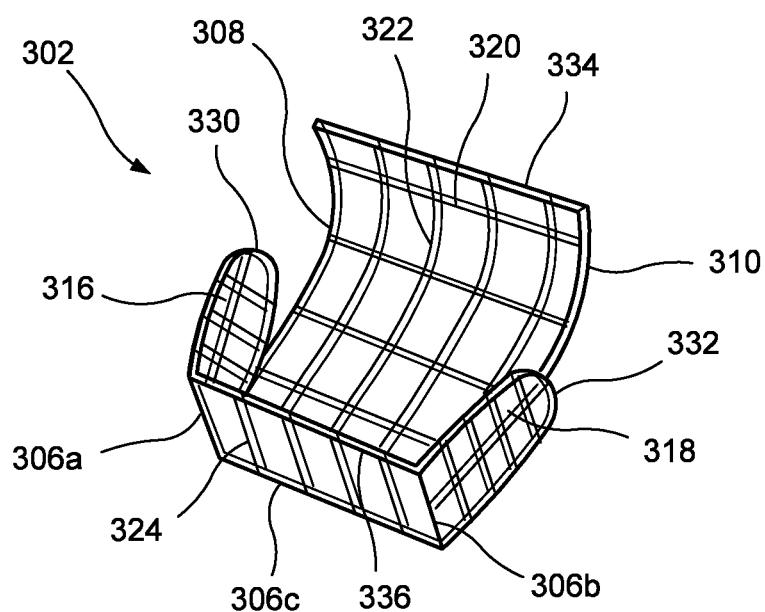
F I G. 8

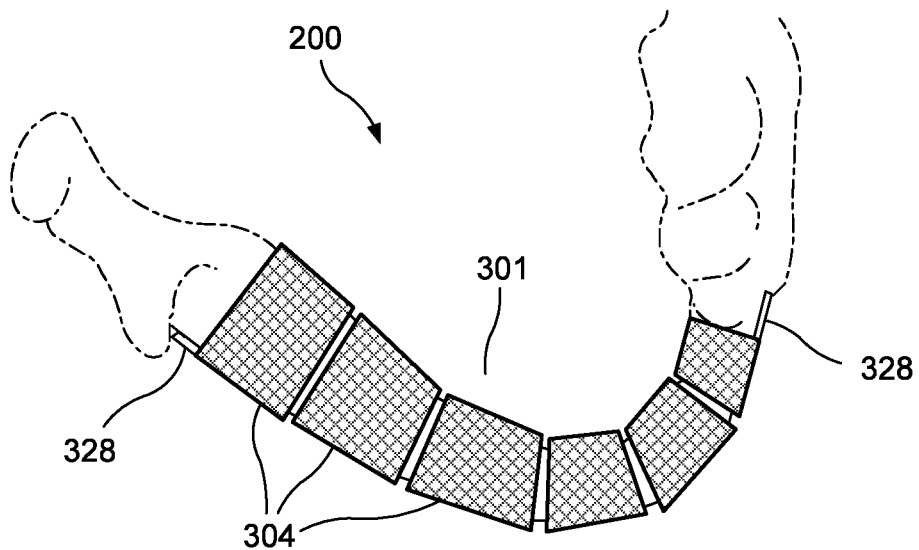
FIG. 9
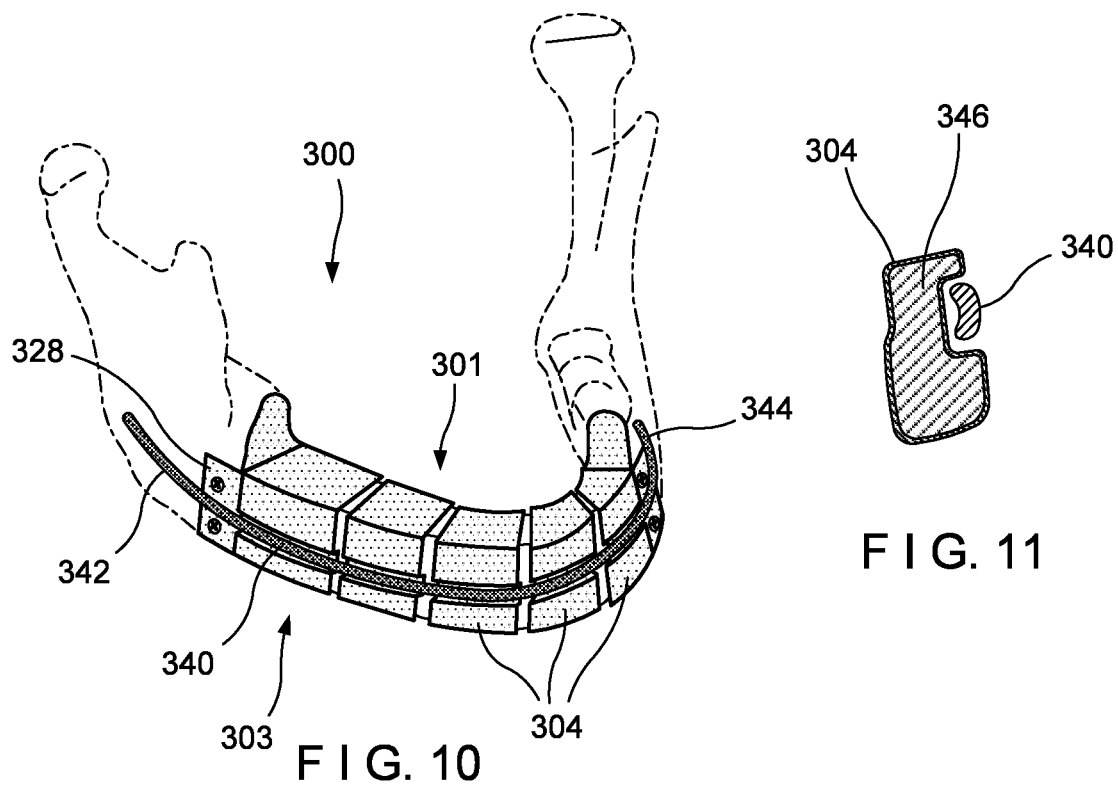
FIG. 10
FIG. 11

FOLD-UP CONTAINMENT DEVICE FOR BONE DEFECTS

PRIORITY CLAIM

The present application is a Divisional Application of U.S. patent application Ser. No. 15/801,528 filed on Nov. 2, 2017; which claims priority to U.S. Provisional Patent Application Ser. No. 62/417,052 filed on Nov. 3, 2016. The entire disclosure of the above patent(s)/application(s) are incorporated herein by reference.

BACKGROUND

Mandible defects are often treated with bone grafts and/or implants such as, bone plates, to assist with healing. The bone grafts may be placed in the target area using any of a variety of methods. However, without a container for the bone graft, the graft may fall away from a target site before it can be incorporated by the body into the healing bone.

SUMMARY

The present disclosure is directed to a bone graft system comprising a two-dimensional mesh sheet sized and shaped to, when folded along fold lines, form a three-dimensional graft containment structure configured to be packed with a bone graft material for placement within a target area of a bone, the mesh sheet including a first end flap connected to a remaining portion of the mesh sheet via a first fold line and a second end flap connected to the remaining portion of the mesh sheet via a second fold line, a third fold line extending from the first fold line to the second fold line so that the remaining portion is configured to be wrapped around folded first and second end flaps to form the graft containment structure, the first and second end flaps substantially corresponding to a profile of the target area of the bone.

The present disclosure is also directed to a bone graft system comprising a graft containment assembly including a plurality of two-dimensional mesh sheets connected to one another along longitudinal edges thereof, each of the mesh sheets sized and shaped so that, when folded along fold lines, each of the mesh sheets form a three-dimensional graft containment structure configured to be packed with a bone graft material, each graft containment structure movable relative to an adjacent graft containment structure to form a desired configuration of the graft containment assembly for placement of the graft containment assembly within a target area of a bone.

The present disclosure also relates to a method for treating a bone comprising folding a first two-dimensional mesh sheet along fold lines to form a first three-dimensional graft containment structure, the first mesh sheet including a first end flap connected to a remaining portion of the mesh sheet via a first fold line and a second end flap connected to the remaining portion of the mesh sheet via a second fold line, a third fold line extending from the first fold line to the second fold line so that the remaining portion is configured to be wrapped around folded first and second end flaps to form the first graft containment structure, packing the first graft containment structure with a bone graft material, maintaining the first graft containment structure in a closed configuration, so that the bone graft material is held therewithin, positioning the first graft containment structure within a target area of a bone, and fixing the first graft containment structure to the bone.

BRIEF DESCRIPTION

FIG. 1 shows a top plan view of a system according to an exemplary embodiment of the present disclosure;

FIG. 2 shows a perspective view of the system of FIG. 1;

FIG. 7 shows a perspective view of a system according to yet another exemplary embodiment of the present disclosure;

FIG. 8 shows a perspective view of a mesh sheet according to the system of FIG. 7;

FIG. 9 shows a top plan view of the system of FIG. 7, in a folded configuration and positioned in a target area of a bone;

FIG. 10 shows a perspective view of the system FIG. 7, in a folded configuration and positioned in the target area of the bone; and FIG. 11 shows a cross-sectional side view of a graft containment structure according to the system of FIG. 7.

DETAILED DESCRIPTION

Figure 3:
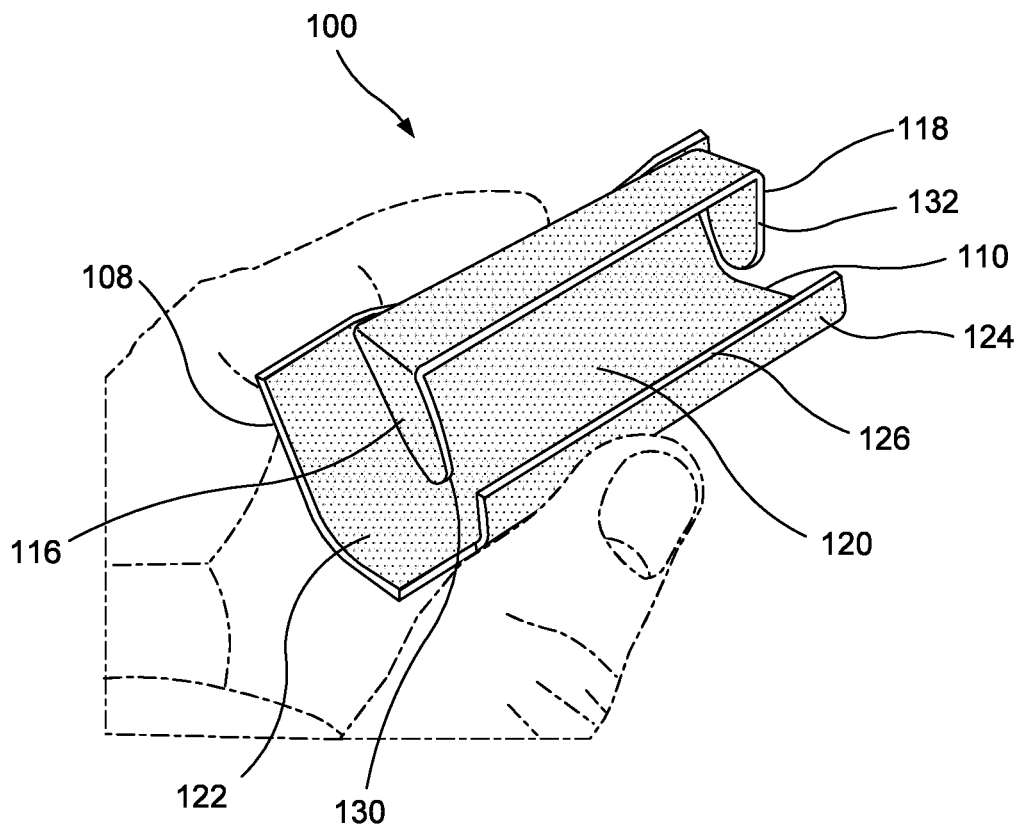
FIG. 3 shows another perspective view of the system of FIG. 1.

The present invention may be understood with reference to the following description and the appended drawings, wherein like elements are referred to with the same reference numerals. The present invention relates to the treatment of bone and, in particular, relates to treatments using bone grafts and bone graft substitutes. Exemplary embodiments of the present invention describe a graft containment cage configured to be positioned in a gap or space in a target bone (e.g., the mandible) so that graft material may be packed therein to encourage and guide the generation of new bone in the gap/space. In one exemplary embodiment, the cage may be positioned between two separated portions of bone to generate new bone joining the separated portions of bone. It will be understood by those of skill in the art, however, that the graft containment cage may be inserted or positioned within any gap or space of the target bone including, for example, at an end of the bone, so that there is bone only on one side of the graft containment cage, or within a recessed space of the bone, so that three sides of the graft containment cage contact bone. The graft containment device of the exemplary embodiment is formed as a two-dimensional mesh sheet that is sized and shaped to be folded-up into a three-dimensional structure that has a shape that substantially corresponds to a shape of a recess or space that is to be filled. Bone graft material or a bone graft substitute material may be packed inside the three-dimensional structure. In one embodiment, the graft containment device is sized, shaped and structure to treat defects of the mandible. Although the exemplary embodiment is shown and described as being used in treating a mandible, it will be understood by those of skill in the art that the graft containment device of the present invention may also be formed in different shapes and sized to permit use in treating other types of bone which would benefit from the use of a graft containment device.

Figure 4:
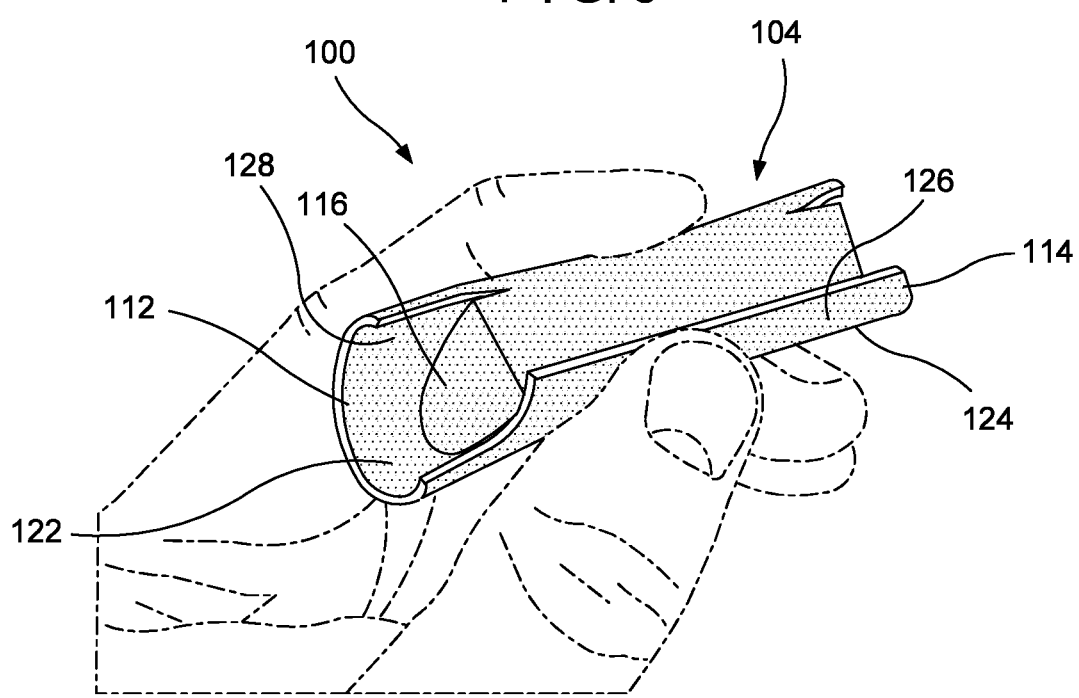
FIG. 4 shows a perspective view of the system of FIG. 1, in a folded configuration.

As shown in FIGS. 1-4, a system 100 according to an exemplary embodiment of the present disclosure comprises a two-dimensional mesh sheet 102 sized and shaped to be folded along fold lines 106, as shown in FIG. 1, to form a three-dimensional graft containment structure 104, as shown in FIG. 4, that is configured to be inserted into a target area of a bone (e.g., to replace a portion of a mandible). The mesh sheet 102 is specifically sized and shaped so that, when folded, the graft containment structure 104 may be positioned in a target area—e.g., a space formerly occupied by bone that has been resected. The target area may, for example, be located ends of a bone on either side of a portion of bone that has been removed. Each of the ends of the graft containment structure 104 may substantially correspond to a profile of an outer surface of a corresponding one of the ends of the separated portions of bone so that the graft containment structure 104 bridges the two separated portions of the bone. Graft material may be packed within an interior of the graft containment structure 104 to promote bone growth between the separated portions of bone as would be understood by those skilled in the art.

The mesh sheet 102, as shown in FIG. 1, includes a plurality of fold lines 106 along which the mesh sheet 102 is specifically configured to be folded to form the graft containment structure 104, as shown in FIG. 4. The mesh sheet 102 defines a first surface 122 which, when the mesh sheet 102 is folded into the graft containment structure 104, forms an interior of the graft containment structure 104, and a second surface 124 which, when the mesh sheet 102 is folded into the graft containment structure 104, forms an exterior of the graft containment structure 104. The mesh sheet 102 also defines a first edge 108 and an opposing second edge 110 such that, when the mesh sheet 102 is folded along the fold lines 106, the resulting graft containment structure 104 extends along a longitudinal axis from a first end 112 corresponding to the first edge 108 to a second end 114 corresponding to the second edge 110. The fold lines 106 may be formed as, for example, living hinges, facilitating folding of the mesh sheet 102 therealong.

In one embodiment, the mesh sheet 102 includes at least three-fold lines 106 which divide the mesh sheet 102 into segments defining distinct surfaces of the graft containment structure 104. The mesh sheet 102 may be shaped to include a first end flap 116 and a second end flap 118, each of which is connected to a remaining portion 120 of the mesh sheet 102 via one of the fold lines 106. In particular, the first end flap 116 is connected to the remaining portion 120 of the mesh sheet 102 via a first one of the fold lines 106a and the second end flap 118 is connected to the remaining portion 120 via a second one of the fold lines 106b. The first and second end flaps 116, 118 may be folded along the first and second fold lines 106a, 106b, respectively, toward the first surface 122. When folded, the first and second end flaps 116, 118 extend transverse to the longitudinal axis of the graft containment structure 104 to define first and second ends 112, 114, respectively, of the graft containment structure 104. In one example, the first and second end flaps 116, 118 fold to extend substantially perpendicular to the longitudinal axis of the graft containment structure 104. As would be understood by those skilled in the art, a shape of each of the first and second end flaps 116, 118 may generally be formed to correspond to a profile of an outer surface of the separated portions of bone.

A third one of the fold lines 106c extends from the first edge 108 to the second edge 110 and connects the first and second fold lines 106a, 106b. Thus, upon folding the mesh sheet 102 along the first and second fold lines 106a, 106b, the mesh sheet 102 may be folded along the third fold line 106c (FIG. 2) and the remaining portion 120 may be wrapped around the folded first and second end flaps 116, 118 (FIG. 3) so that the first surface 122 extends about a perimeter of the first and second end flaps 116, 118, in contact with edges 130, 132, respectively, thereof, to form a substantially closed space within the containment structure 104 (FIG. 4) in which graft material may be held. As would be understood by those of skill in the art the graft containment structure 104 may be filled with graft material during or before folding of the mesh sheet 102. The graft containment structure 104 may be maintained in the closed configuration in any of a variety of ways. For example, the graft containment structure 104 may be closed via suturing and/or hooking.

In a further embodiment, the mesh sheet 102 includes an overlapping portion 126 connected to the remaining portion 120 of the mesh sheet 102 via a fourth fold line 106d. When folded along the fourth fold line, the overlapping portion 126 overlaps a portion of the remaining portion 120 to facilitate closing of the graft containment structure 104. This overlapping portion 126 may be sutured or otherwise attached to the remaining portion 120 to maintain the graft containment structure 104 in the closed configuration, thereby holding the graft material therein.

The mesh sheet 102 may be shaped so that, in one embodiment, upon completion of the folding process, the graft containment structure 104 includes an overhang 128 at each of the first and second ends 112, 114. In other words, a portion of the mesh sheet 102 may extend beyond each of the folded first and second flaps 116, 118 so that, when the graft containment structure 104 is positioned in the target area of the bone, the overhang 128 extends over ends of the separated portions of bone. The overhang 128 may be affixed to the bone via, for example, a bone fixation element, to fix the graft containment structure 104 relative to the bone.

The mesh sheet 102 may be manufactured in a variety of shapes and sizes so that a surgeon or other user may select a desired size and shape most suitable for treating a target bone. In addition or alternatively, a surgeon or other user may trim the mesh sheet 102 to achieve a graft containment structure 104 better suited for the portion of the target bone being treated. For example, portions of the overhang 128 and/or the first and second end flaps 116, 118 may be trimmed to achieve a desired fit. The mesh sheet 102 may include trim lines in the form of, for example, split lines, to guide the proper trimming thereof.

The mesh sheet 102 may be formed of materials such as resorbable polymers (e.g., PCL) or non-resorbable polymers, metals (e.g., titanium) or composites (e.g., graphene, elastomer), depending on an anatomical region being treated and an indication. The mesh sheet 102 may include a plurality of pores extending through the material thereof, the pores shaped to promote vascularization of the bone while preventing graft material packed in the graft containment structure 104 from falling thereoutof. The pores may also be sized and shaped to receive a fixation element therein. In one example, the pores may be sized to receive a fixation screw having a 1.8 mm diameter. In another embodiment, the mesh sheet 102 may be formed via a plurality of intersecting struts formed of a desired material, the struts intersecting to define the pores.

According to an exemplary method, the mesh sheet 102 is configured to be folded along fold lines 106 to form the graft containment structure 104. In particular, the first and second end flaps 116, 118 are folded inward, toward the first surface 122 until the first and second end flaps 116, 118 are substantially perpendicular with respect to the remaining portion 120 of the mesh sheet 102. The remaining portion 120 is wrapped around a perimeter of the first and second end flaps 116, 118 so that the first surface 122 contacts the edges 130, 132 of the first and second flaps, respectively. If so desired, the mesh sheet 102 may be trimmed prior to folding of the mesh sheet 102 to better suit the target area of the bone being treated. Graft material may be packed into the graft containment structure 104 as the mesh sheet 102 is being folded into the desired shape. Once folding of the mesh sheet 102 has been completed, the graft containment structure 104 forms a substantially closed space in which the graft material is held, preventing the graft material from falling thereoutof. Edges and/or surfaces of the mesh sheet 102 which are brought into contact with one another to form the graft containment structure 104 may be sutured, hooked or otherwise affixed to maintain the shape of the graft containment structure.

Once the graft containment structure 104 is in the desired shape and is packed with graft material, as desired, the graft containment structure 104 may be placed in a desired positioned in a recess or gap between two portions of the target bone. For example, the graft containment structure 104 may be positioned such that the first and second ends 112, 114 of the graft containment structure 104 are substantially in alignment with ends separated portions of the bone. The graft containment structure 104 may be further trimmed, if so desired, to aid in positioning of the graft containment structure 104 in the target area of the bone. In one embodiment, overhangs 128 at the first and second ends 112, 114 of the graft containment structure 104 may overlap the ends of the separated portions of bone. These overhangs 128 may be fixed to the bone via, for example, bone fixation elements such as bone screws. The graft containment structure 104 may also be fixed to the bone via a bone plate, extending along a length of the graft containment structure 104 so that ends of the bone plate extend over ends of the separated portions of bone. The bone plate may be fixed both to the graft containment structure 104 and to the bone.

Although the exemplary embodiment describes using a single graft containment structure 104 to treat the target area, multiple graft containment structures 104 may be utilized to treat the target area. This may, however, require trimming of the mesh sheets 102 and/or graft containment structures 104 to fit the target area. In one embodiment, the graft containment structures 104 may be attached to one another, end to end, to form a desired length and/or curvature useful for treating the target area.

Figure 5:
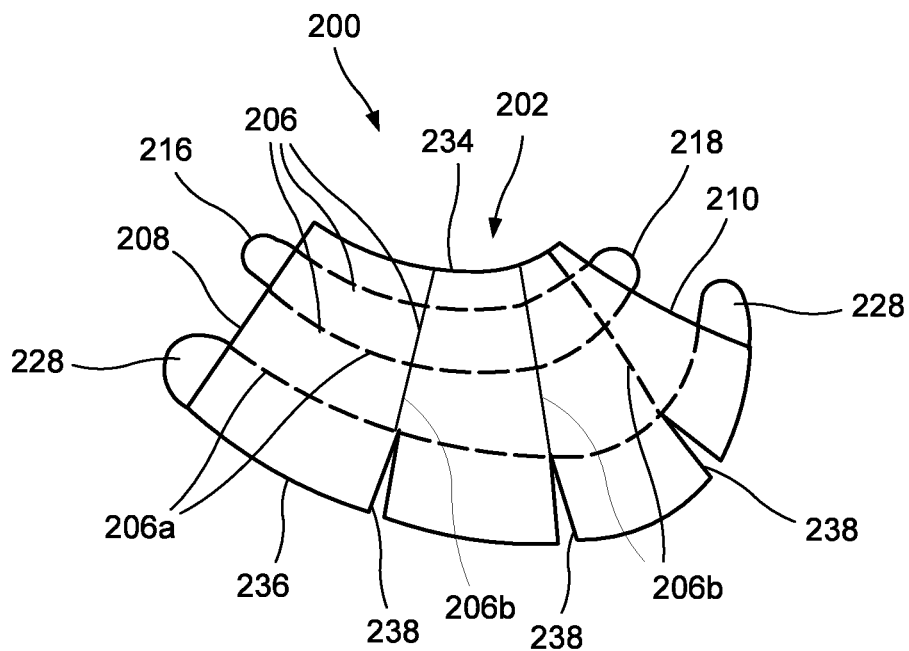
FIG. 5 shows a top plan view of a system according to another exemplary embodiment of the present disclosure.
Figure 6:
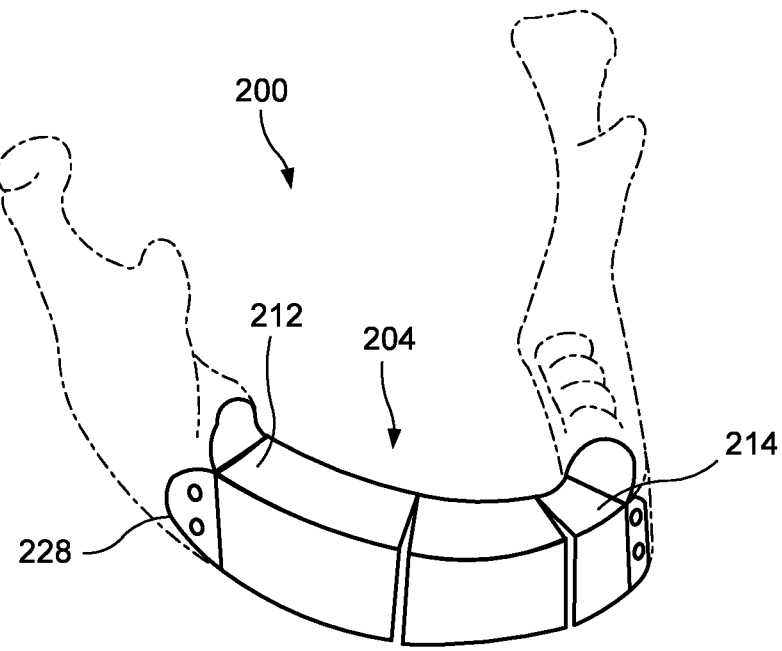
FIG. 6 shows a perspective view of the system of FIG. 5, in a folded configuration.

According to another exemplary embodiment, as shown in FIGS. 5 and 6, a system 200 may be substantially similar to the system 100 described above, comprising a mesh sheet 202 configured to be folded along fold lines 206a, 206b to form a graft containment structure 204. The graft containment structure 204, however, may be specifically designed using a three-dimensional digital environment to match a patient's specific bone dimensions, which may be obtained via, for example, 3D imaging of a target bone. In particular, the 3D scan may be used to generate desired dimensions of the graft containment structure 204 such as, for example, length, curvature, and cross-sectional area. These dimensions are used to design a virtual 3D shape which may then be translated to a digital two-dimensional design to construct a patient-specific mesh sheet 202. The system 200 may use the mesh sheet 102 of the system 100 as a two-dimensional template for the mesh sheet 202. Using the desired dimensions of the graft containment structure 204 and the mesh template, the patient-specific mesh sheet 202 is constructed. The mesh sheet 202 is specifically sized and shaped according to the desired dimensions and is formed to include fold lines 206a, 206b such that, when folded along fold lines 206a, 206b, a graft containment structure 204 having the desired dimensions is formed.

The mesh sheet 202 may be substantially similar to the mesh sheet 102 described above in regard to the system 100. The mesh sheet 202 may include curved longitudinal edges 234, 236 and opposing first and second lateral edges 208, 210 which taper relative to one another as they extend from a first one of the longitudinal edges 234 toward a second one of the longitudinal edges 236. The mesh sheet 202 may also include additional fold lines 206a, 206b and slits 238 along portions thereof to achieve, when folded, a desired curvature and shape of the graft containment structure 204.

In one embodiment, the mesh sheet 202 is particularly constructed to treat a patient's mandible. Similarly to the mesh sheet 102, the mesh sheet 202 includes a first end flap 216 and a second end flap 218 which, when folded, define first and second ends 212, 214, respectively, of the graft containment structure 204. The first and second end flaps 216, 218 are specifically sized and shaped to correspond to a profile of the target area of the mandible of the patient. Longitudinally extending fold lines 206a are designed so that, when folded therealong, the resulting graft containment structure 204 has the desired cross-sectional area for treating the target area of the patient's mandible. The mesh sheet 202 further includes slits 238 extending therealong in alignment with a portion laterally extending fold lines 206b so that, when folded, adjacent portions 240 of the mesh sheet 202, separated from one another via the laterally extending fold lines 206b, may be bent relative to one another to achieve the desired curvature of the graft containment structure 204.

Similarly to the mesh sheet 102, the mesh sheet 202 may also be shaped so that, when folded, the graft containment structure 204 includes overhangs 228 extending beyond the folded first and second end flaps 216, 218. The overhangs 228 may extend over ends of the separated portions of the bone so that the graft containment structure 204 may be fixed to the bone via these overhangs 228.

The system 200 may be utilized in substantially the same manner as described above with respect to the system 100. In particular, the mesh sheet 202 may be folded along fold lines 206a, 206b to construct the patient-specific graft containment structure 204. The graft containment structure 204 may be packed with graft material during the folding of the mesh sheet 202. As described above, the graft containment structure 204 will have a desired size, cross-sectional shape and curvature for treating the target area of the patient.

As shown in FIGS. 7-11, a system 300 may be substantially similar to the systems 100, 200 described above. The system 300, however, comprises a graft containment assembly 301 including a plurality of mesh sheets 302 connected to one another along first longitudinal edges 334 thereof, as shown in FIG. 7. Each of the mesh sheets 302 may be substantially similar to the mesh sheets 102, 202, and may be individually folded to form graft containment structures 304 which, together, form a graft containment device 303 for treating a target area of a patient's bone. Since the mesh sheets 302 are connected along the first longitudinal edges 334, upon folding of the mesh sheets 302, each of the resulting graft containment structures 304 may be positioned/oriented with respect to one another to obtain a desired curvature of the assembly 301 to fit a target area of a bone. Similarly to the system 200, the system 300 may be specifically designed using a three dimensional digital environment to match a patient's specific bone dimensions, which may be obtained via, for example, 3D imaging of a target bone. In particular, the 3D scan may be used to generate desired dimensions of the graft containment assembly 301 such as, for example, length, curvature, and cross-sectional area. These dimensions are then translated to a digital two-dimensional design to construct patient-specific mesh sheet 302, which may be folded to form the desired assembly of graft containment structures 304. Alternatively, the system 300 or any of the embodiments described, may be made in standard sizes which a physician may trim, bend or otherwise customize to suit individual patients in any known manner(s).

Each of the mesh sheets 302, as shown in FIG. 8, may be substantially similar to the mesh sheet 102, described above in regard to the system 100. Each mesh sheet 302 is two-dimensional and is defined via a first surface 322 which, when the mesh sheet 302 is folded toward the graft containment structure 304 forms an interior of the graft containment structure 304, and a second surface 324 which, when the mesh sheet 302 is folded toward the graft containment structure 304 forms an exterior of the graft containment structure. Each mesh sheet 302 may be further defined via first and second longitudinal edges 334, 336 and first and second lateral edges 108, 110. Similarly to the mesh sheet 102, each mesh sheet 302 is sized and shaped to be folded along fold lines 306 to form a desired graft containment structure 304 of the graft containment assembly 301. Each of the graft containment structures 304 may be filled with graft material so that the graft containment assembly 301 may be placed within the target area to promote bone growth and healing. In particular, each mesh sheet 302 a first end flap 316 and a second end flap 318 connected to a remaining portion 320 of each mesh sheet 302 via a first fold line 306a and a second fold line 306b, respectively. When the mesh sheet 302 is folded, the first and second end flaps 316, 318 may form first and second ends 312, 314, respectively, of the graft containment structure 304.

The mesh sheet 302 may include a third fold line 306c along which the remaining portion 320 may be folded to wrap the remaining portion 320 about a perimeter of the first and second end flaps 316, 318. The mesh sheet 302 may be folded to form the graft containment structure 304 in substantially the same was as described above for the system 100. Graft material may be packed within each of the graft containment structures 304 of the assembly 301 during the folding process. Although the exemplary embodiment shows and describes three-fold lines 306, it will be understood by those of skill in the art that the mesh sheets 302 may include more than three-fold lines 306 to form, for example, overlapping portions, similarly to the mesh sheet 102.

It will be understood by those of skill in the art that each of the mesh sheets 302 may have varying sizes and shapes so that a cross-sectional area of the assembly 301 may have a varying size and shape along a length thereof to mimic a naturally changing profile of the bone (e.g., mandible). In particular, first and second end flaps 316, 318 of each of the mesh sheets 302 may vary in size and shape so that the resulting graft containment structures 304 may establish a desired profile within the target area.

Once each of the mesh sheets 302 have been folded and packed with graft material, the graft containment assembly 301 may be positioned, as desired, within the target area of the bone, as shown in FIGS. 9 and 10. Since the mesh sheets 302 are connected to one another along the first longitudinal edges 334, the formed graft containment structures 304 may be positioned and/or oriented with respect to one another (e.g., angled) to form a desired configuration (e.g., curvature) of the assembly 301 suitable for treating the target area. The graft containment assembly may be affixed to separated ends of the bone via, for example, an overhang 328 extending from a first one of the mesh sheets 302a and a last one of the mesh sheets 302b to extend over the separated ends of the bone when the assembly 301 is positioned therein. As shown in FIG. 10, the system 300 may further comprise an implant such as, for example, a bone plate 340 for providing additional fixation. The bone plate 340 may extend across the graft containment structures 304 such that ends 342, 344 thereof extend along the ends of the separated portions of bone. The bone plate 340 may be fixed to each of the graft containment structures 304 to maintain adjacent graft containment structures 304 in a desired position/orientation relative to one another.

As shown in FIG. 11, in a further embodiment, the graft containment structures 304 may be formed with grooves 346 sized and shaped to receive the bone plate 340 therein so that, when the bone plate 340 is placed within the grooves 346 of the graft containment structures 304, the bone plate 340 prevents relative movement between the bone plate 340 and the bone graft containment structures 304 and relative movement between the bone graft containment structures 304 of the assembly 301. In one embodiment, the grooves 346 may be formed via additional fold lines 306 extending along the mesh sheets 302.

It will be understood by those of skill in the art that modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A method for treating mandibular bone, comprising:
    folding a two-dimensional mesh sheet to form a three-dimensional graft containment structure sized and shaped for placement within a target area of a mandibular bone, the mesh sheet including openings sized and shaped to prevent bone graft material from passing therethrough, the folding step including:
        folding a first end flap of the mesh sheet relative to a remaining portion of the mesh sheet at a first fold line;
        folding a second end flap relative to the remaining portion of the mesh sheet via at a second fold line; and
        folding a portion of the mesh sheet along a third fold line extending from the first fold line to the second fold line so that the remaining portion is configured to be wrapped around the folded first and second end flaps to form the three-dimensional graft containment structure, the first and second end flaps substantially corresponding to a profile of the target area of the mandibular bone;
    packing bone graft material in the three-dimensional graft containment structure; and
    positioning the three-dimensional graft containment structure in a space within which mandibular bone growth is desired,
    wherein the two-dimensional mesh sheet is formed to include the first, second, and third fold lines,
    wherein first and second longitudinal edges of the two-dimensional mesh sheet extend along a curve and the two-dimensional mesh sheet includes intersecting longitudinal fold lines and lateral fold lines, wherein the three-dimensional graft containment structure is sized and shaped for replacement of a portion of a mandible.

2. The method of claim 1, wherein the graft containment structure is positioned to replace a missing portion of a mandible.

3. The method of claim 1, wherein the mesh sheet is configured so that, when the mesh sheet has been folded to form the graft containment structure a first overhang extends beyond the folded first end flap, further comprising the step of coupling the first overhang to a portion of bone adjacent to the space within which bone growth is desired.

4. The method of claim 3, wherein the mesh sheet is configured so that, when the mesh sheet has been folded to form the graft containment structure a second overhang extends beyond the folded second end flap, further comprising the step of coupling the second overhang to a portion of bone adjacent to the space within which bone growth is desired.

5. The method of claim 3, wherein the first overhang includes an opening extending therethrough, the opening sized and shaped for receiving a bone fixation element therethrough.

6. The method of claim 1, wherein the mesh sheet includes a plurality of pores extending therethrough, the pores being sized and shaped to promote vascularization therethrough.

7. The method of claim 1, wherein at least one of the first, second and third fold lines comprises a living hinge.

8. The method of claim 1, wherein the mesh sheet includes a lateral fold line a portion of which includes a slit extending therealong so that, when folded, the graft containment structure extends along a curve corresponding to a curvature of a mandible.

9. The method of claim 1, further comprising: closing the graft containment structure by suturing a first portion of the mesh sheet to a second portion of the mesh sheet that was drawn adjacent to the first portion of the mesh sheet by folding.

10. The method of claim 1, further comprising: closing the graft containment structure by hooking a first portion of the mesh sheet to a second portion of the mesh sheet that was drawn adjacent to the first portion of the mesh sheet by folding.

11. The method of claim 1, wherein the mesh sheet is formed of a resorbably polymer.

* * * * *